(12) United States Patent
Park

(10) Patent No.: US 10,773,030 B2
(45) Date of Patent: Sep. 15, 2020

(54) SAFETY SYRINGE

(71) Applicant: C&M Tech Co., Ltd., Chungcheongnam-do (KR)

(72) Inventor: Dae Ryung Park, Chungcheongnam-do (KR)

(73) Assignee: C&M Tech Co., Ltd. (KR)

( * ) Notice: Subject to any disclaimer, the term of this patent is extended or adjusted under 35 U.S.C. 154(b) by 77 days.

(21) Appl. No.: 15/826,982

(22) Filed: Nov. 30, 2017

(65) Prior Publication Data

US 2019/0030259 A1     Jan. 31, 2019

(30) Foreign Application Priority Data

Jul. 28, 2017 (KR) .......................... 10-2017-0096056
Nov. 10, 2017 (KR) .......................... 10-2017-0149090

(51) Int. Cl.
    *A61M 5/32*          (2006.01)
    *A61M 5/315*          (2006.01)
    *A61M 5/31*          (2006.01)
    *A61M 5/50*          (2006.01)

(52) U.S. Cl.
    CPC ........ *A61M 5/3257* (2013.01); *A61M 5/3145* (2013.01); *A61M 5/31513* (2013.01); *A61M 5/502* (2013.01); *A61M 2005/3128* (2013.01); *A61M 2205/0216* (2013.01)

(58) Field of Classification Search
    CPC .. A61M 2005/3128; A61M 2005/3267; A61M 2205/0216; A61M 25/0625; A61M 2005/31523
    See application file for complete search history.

(56) References Cited

U.S. PATENT DOCUMENTS

| | | | | |
|---|---|---|---|---|
| 5,106,379 | A | * | 4/1992 | Leap ................... A61M 5/3271 604/198 |
| 6,053,894 | A | * | 4/2000 | Shadd, Jr. .......... A61M 5/31511 604/110 |
| 2003/0144630 | A1 | * | 7/2003 | Chang ................. A61M 5/3272 604/198 |
| 2004/0138611 | A1 | * | 7/2004 | Griffiths ............ A61M 5/31596 604/82 |
| 2010/0324502 | A1 | * | 12/2010 | Guala ................. A61M 5/3134 604/236 |
| 2011/0046561 | A1 | * | 2/2011 | Pickhard ............... A61M 5/322 604/190 |
| 2015/0065992 | A1 | * | 3/2015 | Korkuch ............ A61M 5/3145 604/506 |

\* cited by examiner

*Primary Examiner* — Tiffany Legette
(74) *Attorney, Agent, or Firm* — Mendelsohn Dunleavy, P.C.

(57) ABSTRACT

Disclosed is a safety syringe capable of preventing needle-stick injuries, filtering foreign matters in a fluid, and preventing reuse thereof. The safety syringe includes: a safety needle part provided with a safety cap, the safety cap being configured to pop out by an elastic force of an elastic body connected thereto when the safety cap is unlatched and to be fixed while surrounding a needle tip; a filter part being configured such that a first end thereof is coupled with the safety needle part, and filtering fluid introduced or discharged through the needle; and a main body part being configured such that a first end thereof is coupled with the filter part, and having a barrel with a piston mounted therein, the piston being provided at a fore end thereof with an insertion part pushing out the fluid by being inserted into a luer of the syringe.

10 Claims, 14 Drawing Sheets

(a)         (b)

(a)

(b)

(a)  (b)  (c)  (d)

10,773,030 B2

SAFETY SYRINGE

CROSS REFERENCE TO RELATED APPLICATION

The present application claims priority to Korean Patent Application Nos. 10-2017-0096056 and 10-2017-0149090, filed on Jul. 28, 2017 and Nov. 10, 2017 respectively, the entire contents of which is incorporated herein for all purposes by this reference.

BACKGROUND OF THE INVENTION

Field of the Invention

The present invention relates generally to a syringe. More particularly, the present invention relates to a safety syringe capable of preventing needle-stick injuries because of carelessness after injecting fluid to a patient, capable of filtering foreign matters contained in a fluid, and capable of preventing reuse thereof.

Description of the Related Art

Syringes used as a means of injecting drugs to patients for treatment require great care in handling. Since the fluid is injected by sticking the needle into the blood vessel of the patient, the syringe used once has to be disposed of because of the risk of infection.

However, in some unscrupulous hospitals, the used syringes are often reused, which is sometimes a social problem.

Because the needle is very sharp, it requires a high degree of care during handling, but even the medical staff may be accidentally pricked by the used needle, resulting in a secondary infection of the disease.

Further, if the fluid contains foreign matters such as microscopic glass debris, they may enter the patient's veins at the time of injection.

Further, the syringe has to be discarded after a single use so that there may be some fluid left in the syringe, which causes waste of fluid.

As one conventional art relating to the present invention, in the document of Korean Patent No. 10-1448858, "Capping apparatus of needle for syringe" has been disclosed.

FIG. 1 shows a perspective view of a capping apparatus of a needle for a syringe according to the conventional art.

As shown in the drawing, the capping apparatus of a needle for a syringe includes: a needle holder provided with a needle of a syringe and detachably coupled to the syringe, and formed with a guide part on an outer circumferential surface thereof; a link configured to move along the guide part in a longitudinal direction of the needle; a switch part configured to move along the link in the longitudinal direction of the needle and provided with a protection part to cover an end portion of the needle; and an elastic body arranged between the needle holder and the switch part and configured to provide operating power to move the switch part in order for the protection part to cover the end portion of the needle.

The switch part 400 includes a cap portion 420, a stop portion 430, and a rod portion 440, wherein when a user pushes the stop portion 430 upward, the stop state is released, and the cap portion 420 is moved upward by an elastic force of a spring, thereby covering a needle tip.

However, since the rod portion is moved upward along the link 300, the cap portion 420 and the center axis of the needle 201 correspond with each other, so when the cap portion 420 is pressed, the needle 201 may protrude again, thereby causing needle-stick injuries.

Further, when the cap portion 420 covers the needle tip, the needle in the spring is exposed as it is, which may cause user anxiety.

In this regard, the capping apparatus prevents needle-stick injuries, but there is a need to improve safety.

As another conventional art relating to the present invention, in the document of Korean Patent No. 10-1742803, "Safety syringe" has been disclosed.

The conventional safety syringe is configured such that fluid passes a filter only when it is discharged. Accordingly, there may be some foreign matters left unfiltered.

Further, even though the piston is pushed to the end, a gap is famed between the inside of a filter body and a fore end of the piston, whereby the fluid is left.

Further, the conventional safety syringe is problematic in that in order to prevent reuse, the piston is pulled backward to move the needle inside the barrel, and then the user bends the piston on purpose. As such, the conventional safety syringe needs to be improved.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and the present invention is intended to propose a safety syringe having a simple structure to prevent needle-stick injuries after use of the syringe, and being provided with a safety cap easy to handle.

In particular, the present invention is intended to propose a safety syringe configured such that after the safety cap is operated to cover the needle of the used syringe, the needle in a spring is not exposed to the outside, whereby it is possible to further improve safety.

The present invention is further intended to propose a safety syringe, which is provided with a double filter that can completely block foreign matters contained in the fluid.

The present invention is further intended to propose a safety syringe configured such that a fore end of a piston is provided with a protrusion, and the protrusion is engaged with the inside of a luer of the syringe so as not to be separated from each other, whereby it is possible to reduce the amount of the fluid remaining in the syringe, and it is possible to prevent reuse of the syringe.

The present invention is further intended to propose a safety syringe, which is modularized into a safety needle part, a filter part, and a main body part, respectively, whereby it is possible to assemble by selecting a module according to the customer's request.

In order to achieve the above object, according to one aspect of the present invention, there is provided a safety syringe including: a safety needle part provided with a safety cap, the safety cap being configured to pop out by an elastic force of an elastic body connected thereto when the safety cap is unlatched and to be fixed while surrounding a needle tip; a filter part being configured such that a first end thereof is coupled with the safety needle part, and filtering fluid introduced or discharged through the needle; and a main body part being configured such that a first end thereof is coupled with the filter part, and having a barrel with a piston mounted therein, the piston being provided at a fore end thereof with an insertion part pushing out the fluid by being inserted into a luer of the syringe.

Preferably, the safety needle part includes: a needle hub fastening a lower portion of the needle; a safety holder with the needle hub mounted therein, the safety holder configured such that a lower outer surface thereof is provided with a latching protrusion and an upper outer surface thereof is provided with a fastening protrusion; a safety cap configured such that a latching means corresponding to the latching protrusion is provided at a first end thereof, a fastener corresponding to the fastening protrusion is provided above the latching means, and a through-hole is provided at a second end thereof to allow the needle to pass therethrough; and the elastic body configured such that a first end thereof is connected with the safety holder and a second end thereof is connected with the safety cap.

Preferably, in order to unlatch the safety cap, the latching means is disengaged from the latching protrusion by a pressing force pressing the latching protrusion or by rotating the safety cap.

Preferably, as the safety cap pops out, the fastening protrusion of the safety holder and the fastener of the safety cap are coupled to each other such that the safety cap is fixed to the safety holder while surrounding the needle tip.

Preferably, the filter part is provided with a double filter, wherein the double filter is coupled with the barrel in which the piston mounted, and is provided with an inlet port through which the fluid is introduced in the barrel, and an outlet port through which the fluid in the barrel is discharged, thereby performing double filtering.

Preferably, the filter part includes: a filter housing configured such that a first end thereof is connected with the safety needle part and a second end thereof is coupled with the main body part; the double filter mounted in the filter housing, and provided with the inlet port and the outlet port that are opened in opposite directions; and a filter provided in each of the inlet port and the outlet port.

Preferably, the double filter is made of silicone and is constituted by an integral or separate valve, and each of the inlet port and the outlet port is provided with a valve configured to be opened in one direction.

Preferably, a serration is formed on an inner surface of a first end of the safety holder, and a concave-convex portion is formed on an outer surface of the first end of the filter housing to correspond to the serration, whereby the safety holder and the filter housing are coupled to each other, and after being coupled, the safety holder and the filter housing are prevented from being rotated in opposite directions.

Preferably, a lower portion of the safety holder is provided with an anti-vertical moving means, and an upper outer surface of the filter housing is provided with an anti-vertical moving protrusion, whereby the safety holder and the filter housing are coupled to each other, and after being coupled, the safety holder and the filter housing are prevented from being moved vertically.

Preferably, a serration is formed on an inner surface of the first end of the filter housing, and a concave-convex portion is formed on an outer surface of a locking portion provided at a first end of the barrel to correspond to the serration, whereby the filter housing and the barrel are coupled to each other, and after being coupled, the filter housing and the barrel are prevented from being rotated in opposite directions.

Preferably, the main body part includes: the barrel receiving the fluid introduced through the needle; the piston mounted in the barrel and provided with the insertion part at a fore end thereof to push out the fluid by being inserted into the luer at the upper portion of the barrel; and a gasket of elastic material surrounding the fore end of the piston with the insertion part penetrating therethrough.

Preferably, the insertion part includes a cylindrical body with a conical tip formed at a first end of the cylindrical body such that a longitudinal section of the insertion part is in a form of an arrow, and a diameter of a bottom of the conical tip is larger than a diameter of an opening of the luer from which the conical tip is inserted; a stop step is provided inside the luer; and when the piston is pressed forward strongly, the bottom of the conical tip passes through the stop step and is stopped by the stop step.

Preferably, the gasket is provided with at least one coupling groove thereinside, and the fore end of the piston is formed with a coupling protrusion corresponding to the coupling groove, whereby the coupling groove and the coupling protrusion are engaged with each other, and after the bottom of the conical tip is stopped by the stop step, when the piston is pulled backward strongly, a thinnest portion of the piston below the insertion part is broken.

In order to achieve the above object, according to another aspect of the present invention, there is provided a safety syringe including: a safety needle part provided with a safety cap, the safety cap being configured to pop out by an elastic force of an elastic body connected thereto when the safety cap is unlatched and to be fixed while surrounding a needle tip; and a main body part being configured such that a first end thereof is coupled with the filter part, and having a barrel with a piston mounted therein, the piston being provided at a fore end thereof with an insertion part pushing out the fluid by being inserted into a luer of the syringe, wherein once the safety needle part and the main body part are coupled to each other, the safety needle part and the main body part are prevented from being separated from each other.

In order to achieve the above object, according to a further aspect of the present invention, there is provided a safety syringe including: a filter part filtering fluid introduced or discharged through a needle of the syringe; and a main body part being configured such that a first end thereof is coupled with the filter part, and having a barrel with a piston mounted therein, the piston being provided at a fore end thereof with an insertion part pushing out the fluid by being inserted into a luer of the syringe, wherein once the filter part and the main body part are coupled to each other, the filter part and the main body part are prevented from being separated from each other.

According to the present invention, since the safety syringe of the present invention is configured such that the needle of the used syringe is covered with the safety cap, and the needle cannot be separated from the safety cap even when an external force is applied thereto, it is possible to prevent secondary infection by being pricked by the used needle.

In particular, since the safety syringe of the present invention is configured such that after the safety cap is operated to cover the needle of the used syringe, the needle in the spring is not exposed to the outside, it is possible to further improve safety.

Further, since the safety syringe of the present invention is provided with the double filter, it is possible to prevent harmful matters from being injected into the blood vessel.

Further, since the safety syringe of the present invention is configured such that a fore end of the piston is provided with a protrusion, and the protrusion is engaged with the inside of the luer of the syringe so as not to be separated from each other, it is possible to reduce the amount of the fluid remaining in the syringe, and it is possible to prevent reuse of the syringe.

Further, since the safety syringe of the present invention is configured such that components constituting the syringe are integrally provided so as not to be easily separated from each other, it is possible to prevent reuse of the used syringe.

Further, since the safety syringe of the present invention is modularized into the safety needle part, the filter part, and the main body part, respectively, it is possible to assemble by selecting a module according to the customer's request.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, a safety syringe according to the present invention will be described in detail with reference to the accompanying drawings.

The safety syringe of the present invention includes: at least one of a safety needle part provided with a safety cap, the safety cap configured to pop out by an elastic force of an elastic body connected thereto when the safety cap is unlatched and be fixed while surrounding a needle tip, and a filter part being connected with the needle of the syringe and filtering fluid introduced or discharged through the needle; and a main body part coupled with a barrel with a piston mounted therein, the piston provided at a fore end thereof with an insertion part pushing out the fluid by being inserted into a luer of the syringe.

In other words, the safety syringe of the present invention may include all of the safety needle part, the filter part, and the main body part, may include the safety needle part and the main body part of the above three parts, or may include the filter part and the main body part. Accordingly, depending on the buyer's request, only some of the three parts can be selected and assembled.

Firstly, the safety syringe according to a first embodiment of the present invention includes all of the safety needle part, the filter part, and the main body part.

Figure 1:
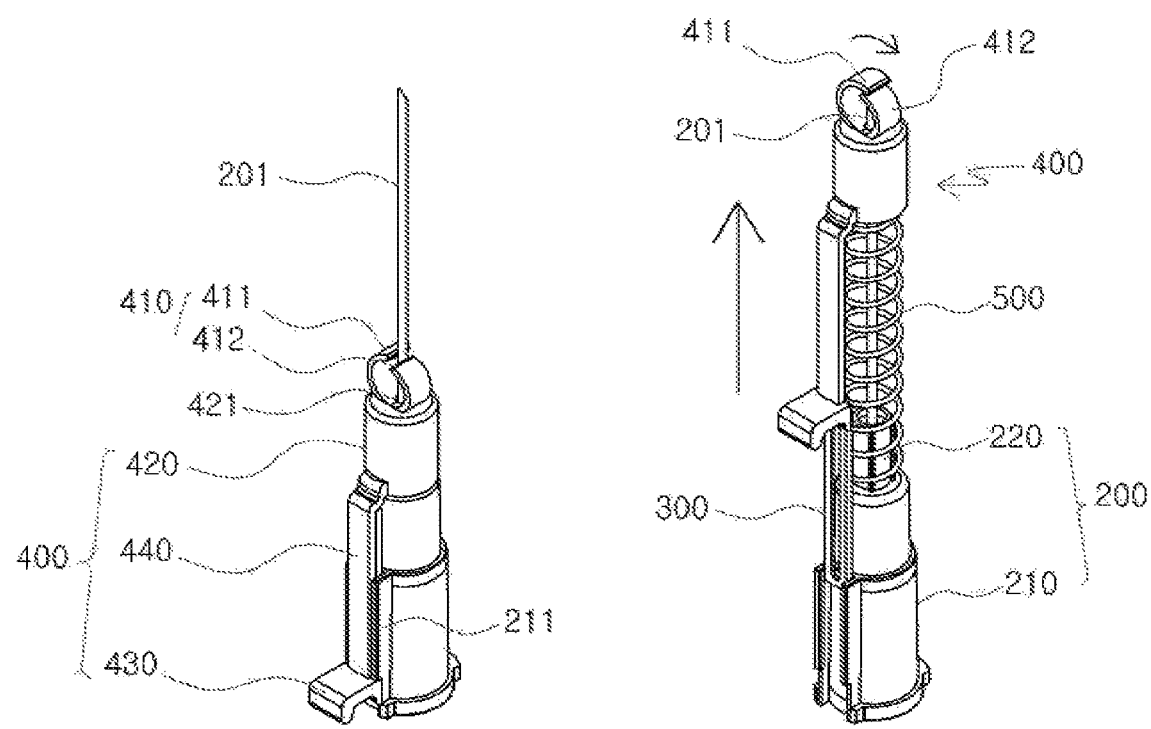
FIG. 1 shows a perspective view of a capping apparatus of a needle for a syringe according to the conventional art.
Figure 2:
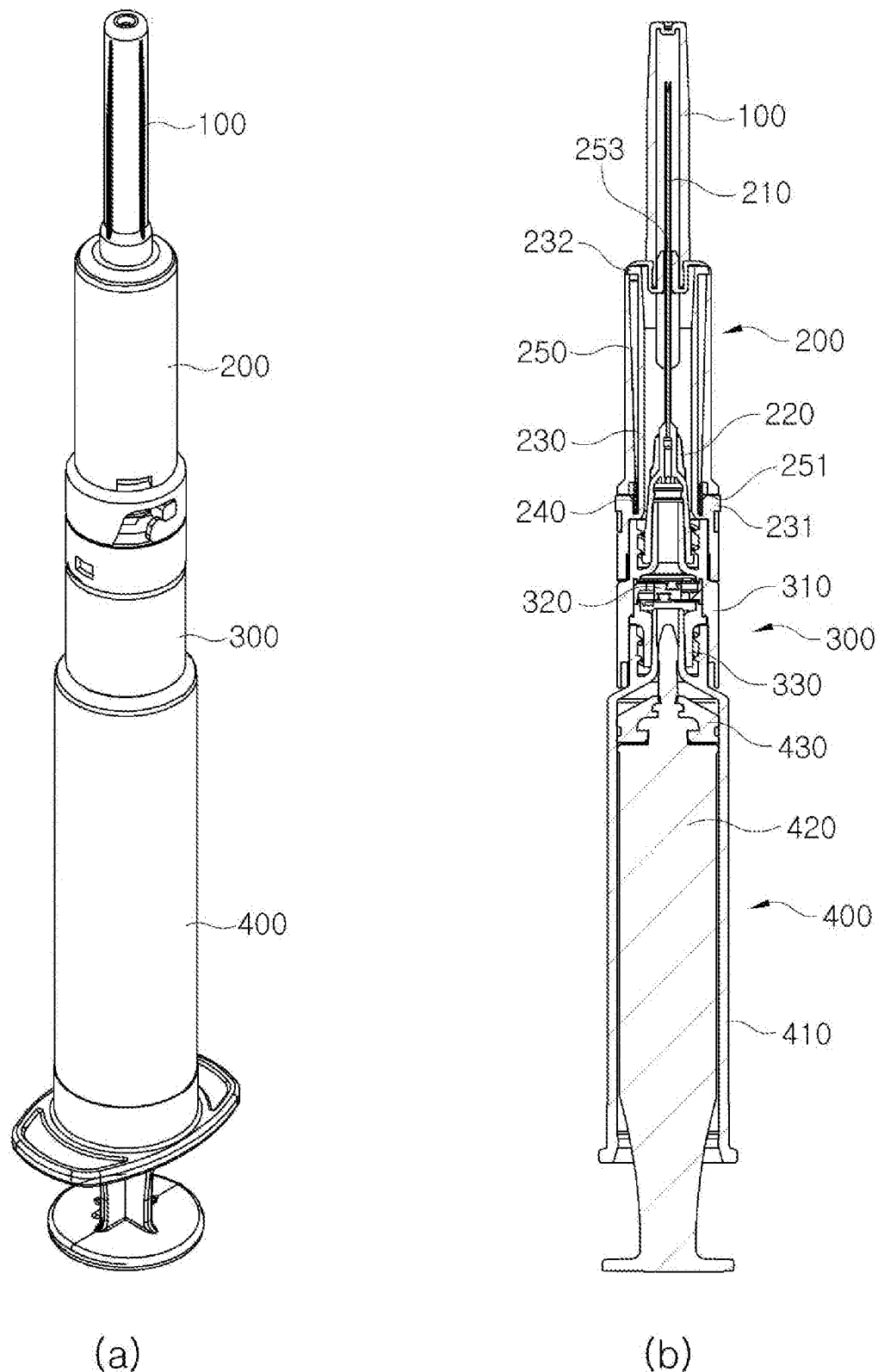
FIG. 2 shows a perspective view and a sectional view of a safety syringe according to a first embodiment of the present invention.
Figure 3:
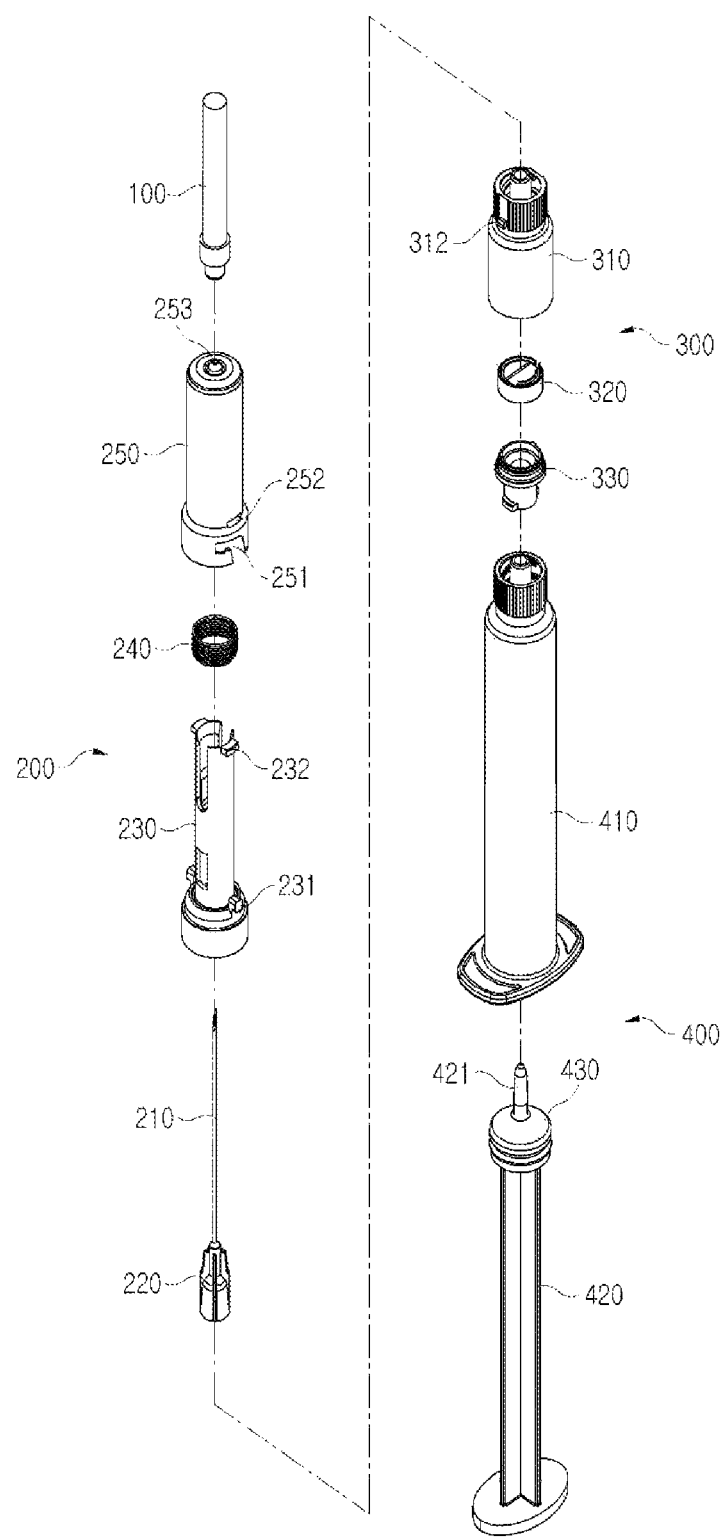
FIG. 3 shows an exploded perspective view of the safety syringe according to the first embodiment of the present invention.
Figure 4:
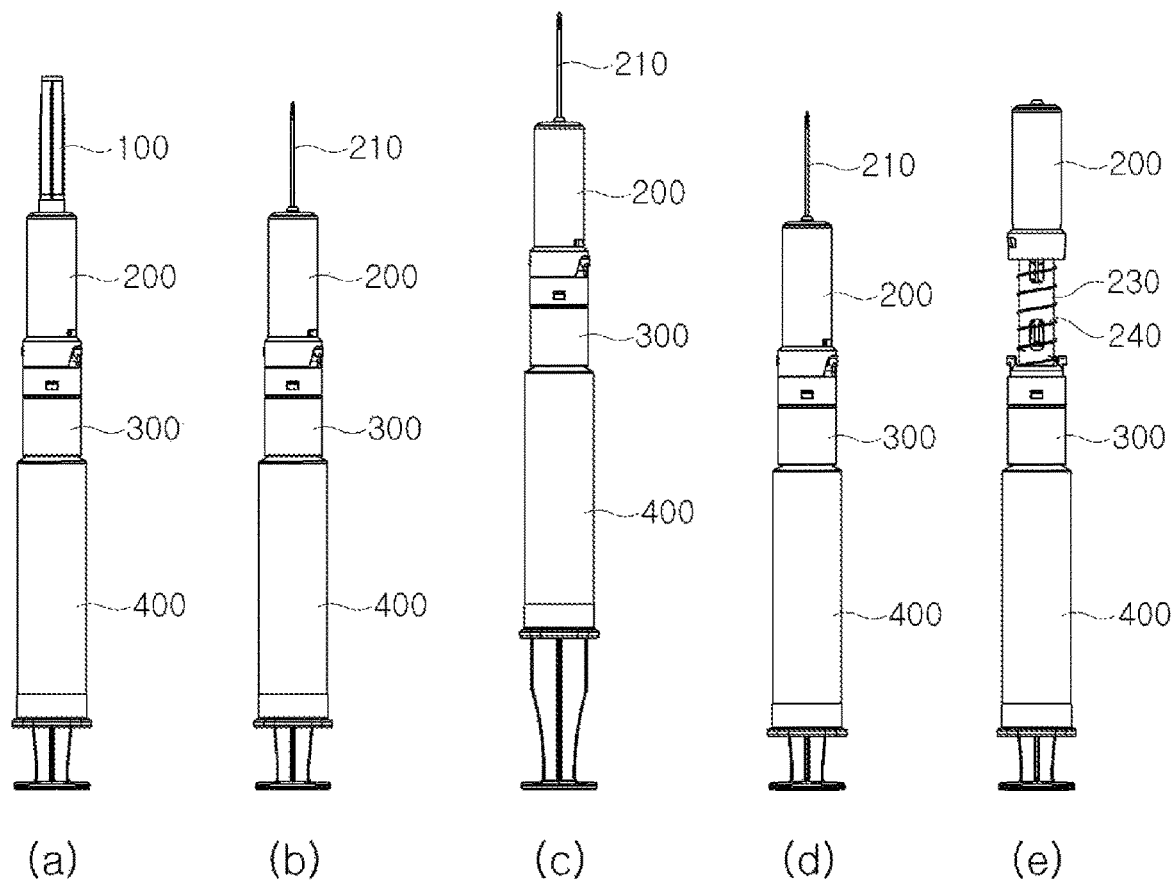
FIG. 4 shows use state views of the safety syringe according to the first embodiment of the present invention.
Figure 5:
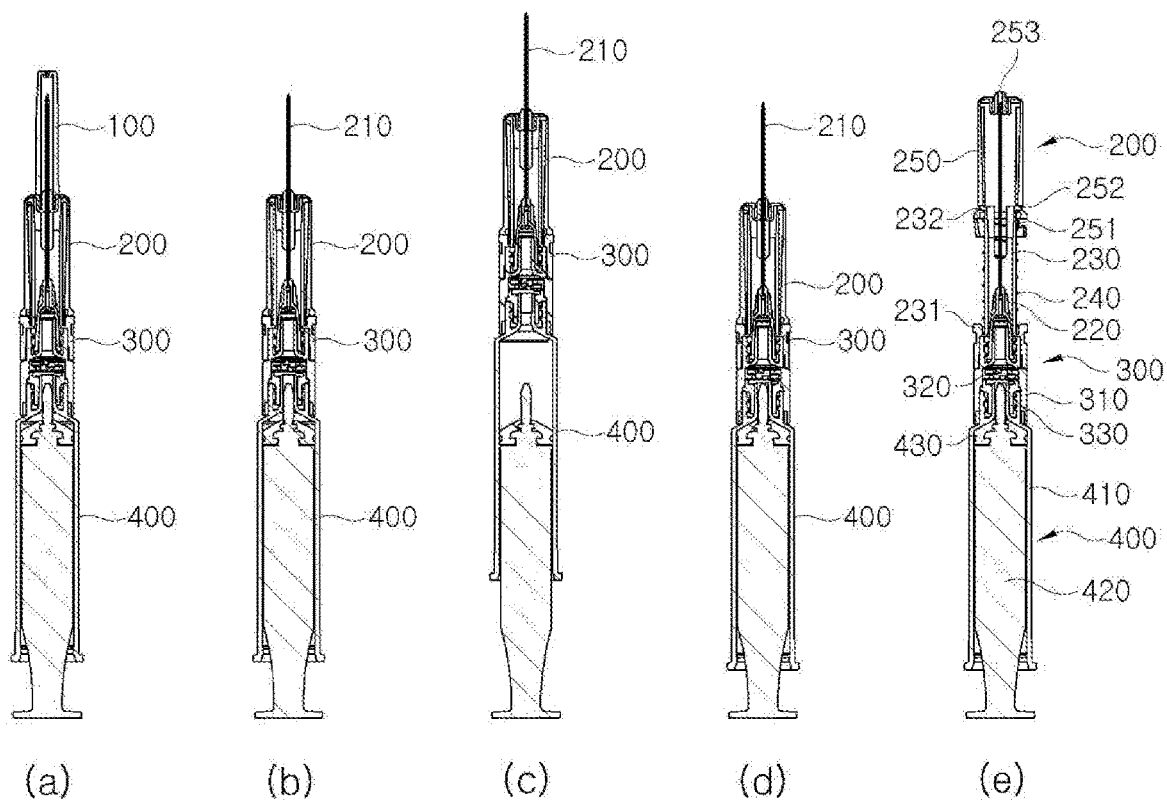
FIG. 5 shows sectional use state views of the safety syringe according to the first embodiment of the present invention.
Figure 6:
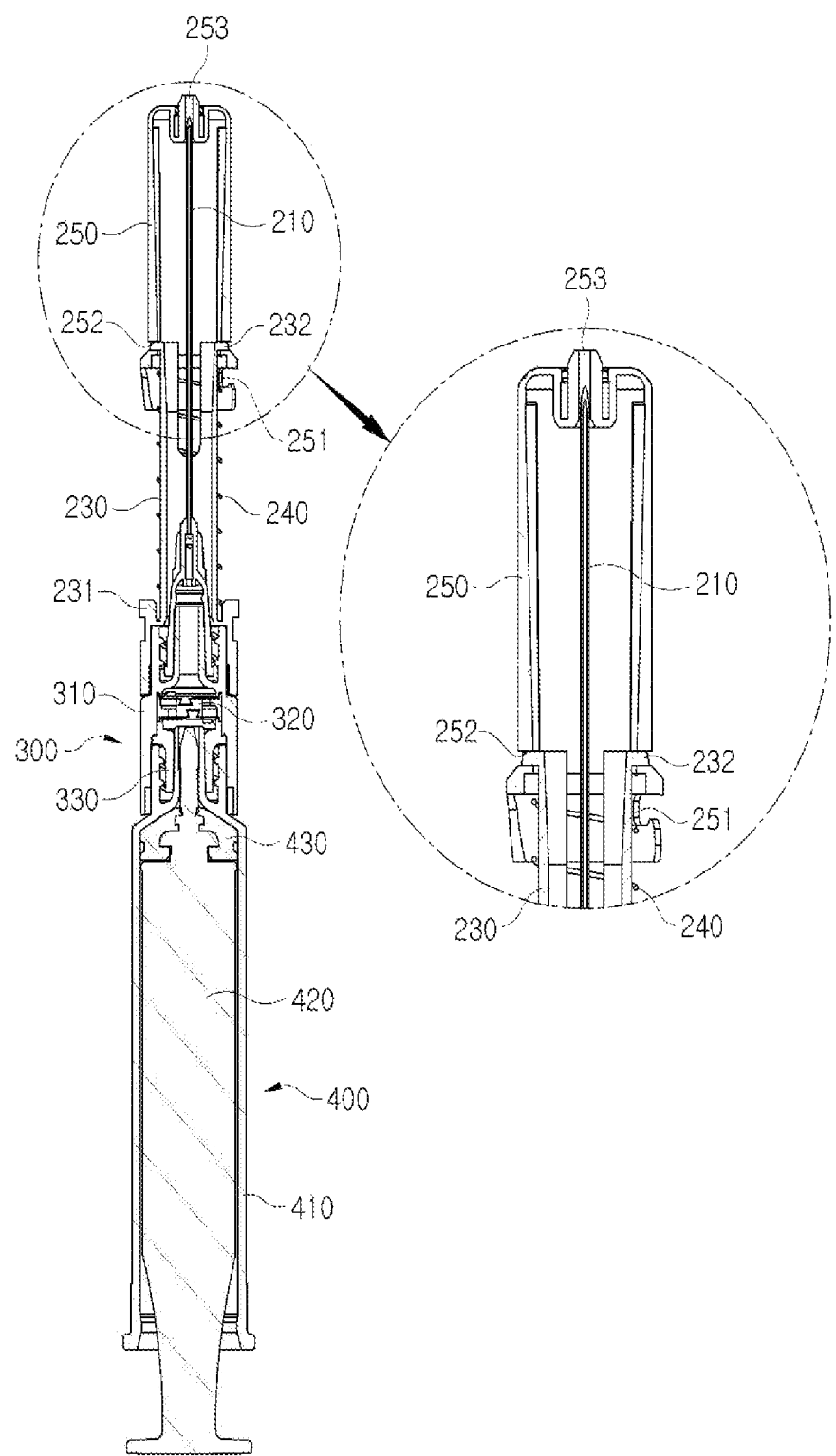
FIG. 6 shows an enlarged sectional view of a safety cap popping out and a safety holder.
Figure 7:
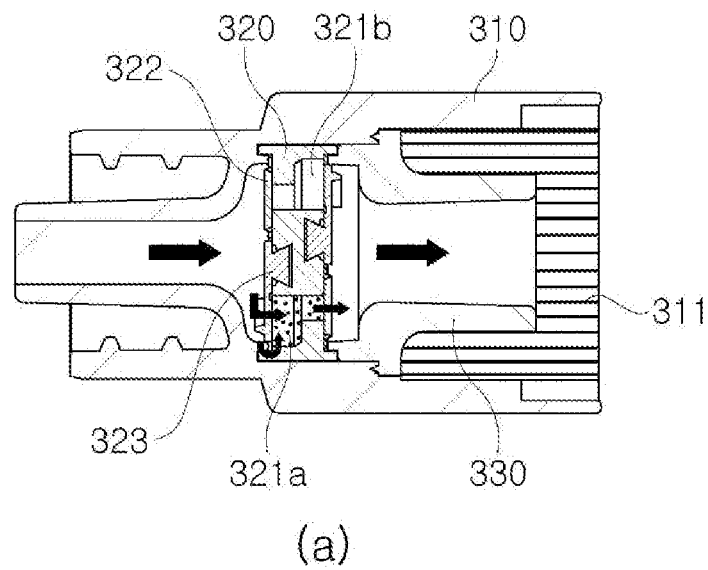
FIG. 7 shows exemplary views of a process where fluid is introduced and discharged in a filter part.
Figure 7:
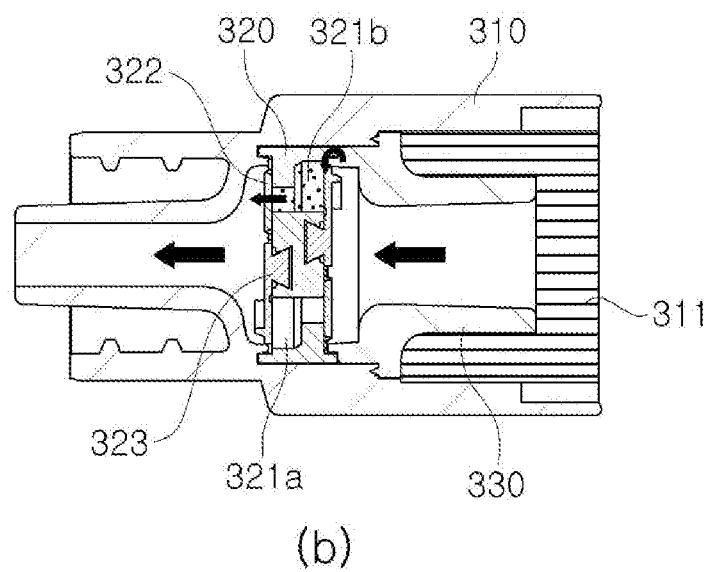
Figure 8:
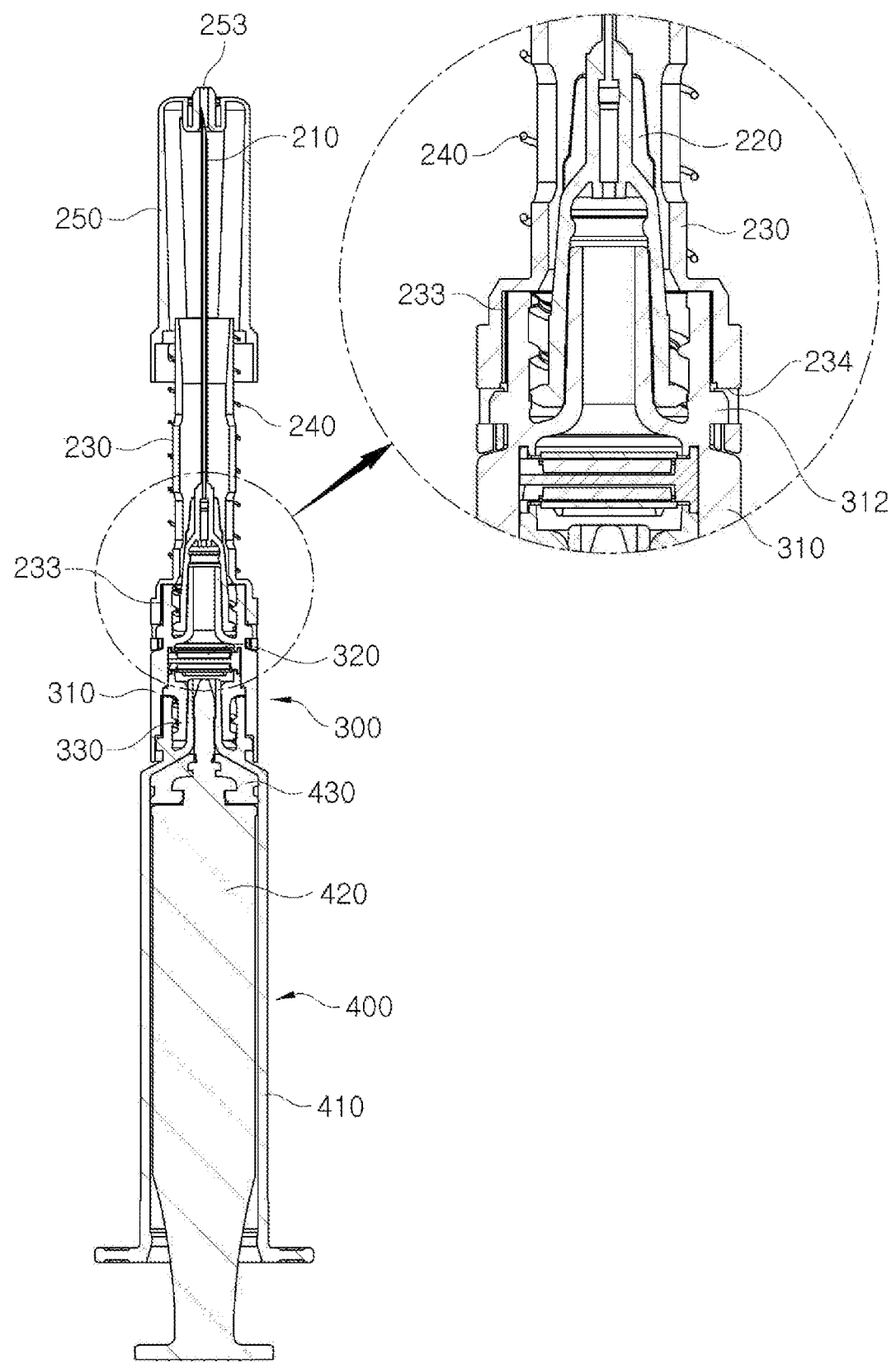
FIG. 8 shows an enlarged sectional view of a portion where a safety needle part and a filter part are connected with each other.
Figure 9:
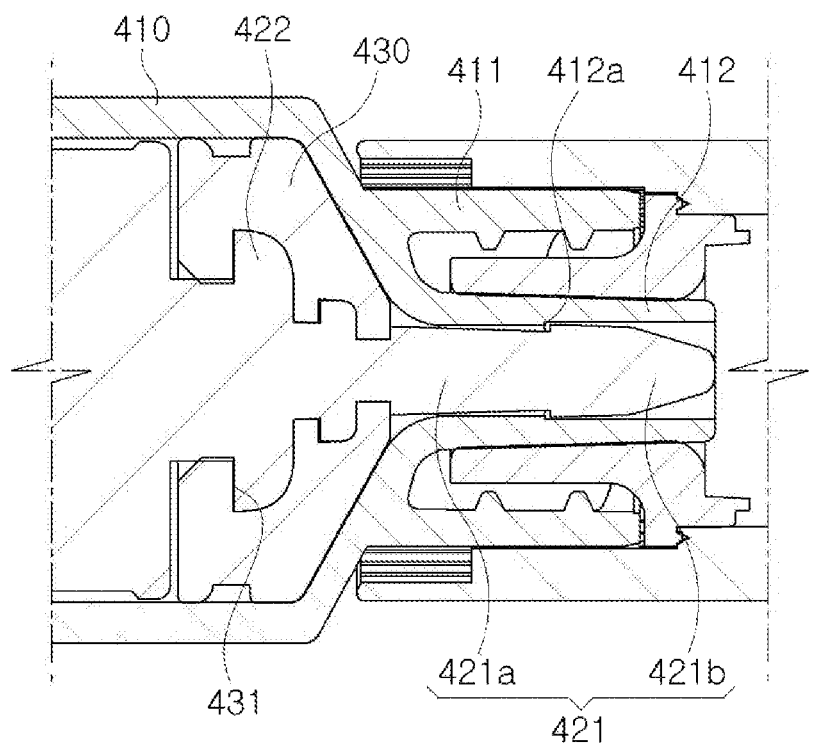
FIG. 9 shows an enlarged sectional view of an insertion part of a piston and an inside of a luer.
Figure 10:
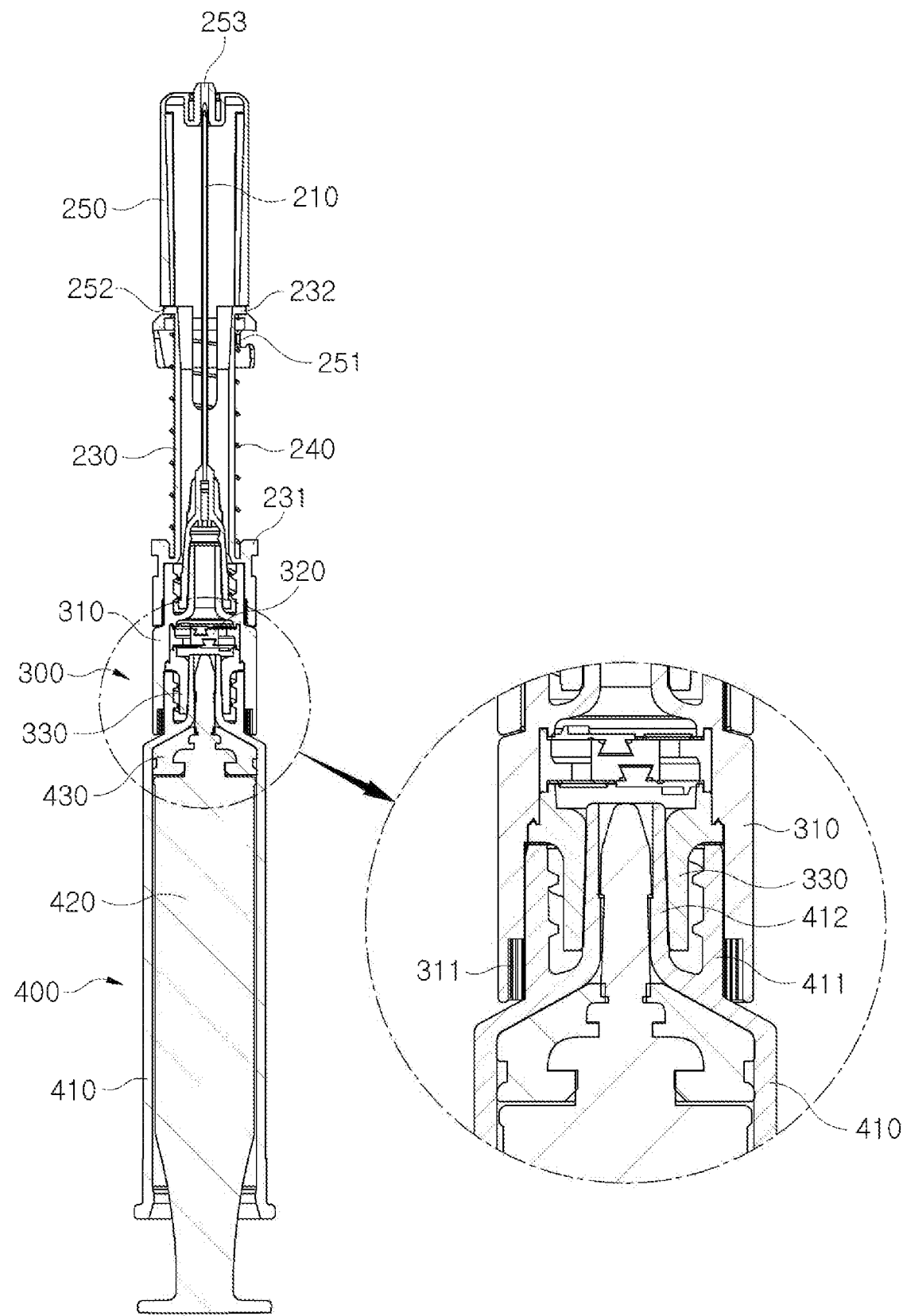
FIG. 10 shows an enlarged sectional view of a portion where the filter part and a main body part.

FIG. 2 shows a perspective view and a sectional view of a safety syringe according to a first embodiment of the present invention; FIG. 3 shows an exploded perspective view of the safety syringe according to the first embodiment of the present invention; FIG. 4 shows use state views of the safety syringe according to the first embodiment of the present invention; FIG. 5 shows sectional use state views of the safety syringe according to the first embodiment of the present invention; FIG. 6 shows an enlarged sectional view of a safety cap popping out and a safety holder; FIG. 7 shows exemplary views of a process where fluid is introduced and discharged in a filter part; FIG. 8 shows an enlarged sectional view of a portion where a safety needle part and a filter part are connected with each other; FIG. 9 shows an enlarged sectional view of an insertion part of a piston and an inside of a luer; and FIG. 10 shows an enlarged sectional view of a portion where the filter part and a main body part.

Hereinbelow, the first embodiment of the present invention will be described in detail with reference to FIGS. 2 to 10.

As shown in FIG. 2, in general, the safety syringe is initially provided with a needle 210 capped with a needle cap 100, and is used after removing the needle cap 100.

The safety syringe according to the first embodiment of the present invention includes: a safety needle part 200 provided with a safety cap 250, the safety cap configured to pop out by an elastic force of an elastic body when the safety cap is unlatched and be fixed while surrounding a needle tip; a filter part 300 being configured such that a first end thereof is coupled with the safety needle part 200, and filtering fluid introduced or discharged through the needle 210; and a main body part 400 being configured such that a first end thereof is coupled with the filter part 300, and having a barrel 410 with a piston 420 mounted therein, the piston provided at a fore end thereof with an insertion part 421 pushing out the fluid by being inserted into a luer of the syringe.

Firstly, the safety needle part 200 includes: a needle hub 220 fastening a lower portion of the needle 210; a safety holder 230 with the needle hub 220 mounted therein, the safety holder configured such that a lower outer surface thereof is provided with a latching protrusion 231 and an upper outer surface thereof is provided with a fastening protrusion 232; a safety cap 250 configured such that a latching means 251 corresponding to the latching protrusion 231 is provided at a first end thereof, a fastener 252 corresponding to the fastening protrusion 232 is provided above the latching means 251, and a through-hole 253 is provided at a second end thereof to allow the needle 210 to pass therethrough; and the elastic body 240 configured such that a first end thereof is connected with the safety holder 230 and a second end thereof is connected with the safety cap 250.

In particular, the safety cap 250 constituting the safety needle part 200 is latched by the latching protrusion 231 of the safety holder 230 before use of the syringe, and when the safety cap is unlatched to surround the exposed needle 210 after use of the syringe, the safety cap 250 pops out by the elastic force of the elastic body 240 such as a spring and is moved forward, thereby surrounding the sharp needle tip.

More preferably, in order to unlatch the safety cap 250, the latching protrusion 231 may be disengaged from the latching means 251 by a pressing force, or the latching means 251 may be released from the latching protrusion 231 by rotating the safety cap 250.

More preferably, as the safety cap 250 pops out, the fastening protrusion 232 of the safety holder 230 and the fastener 252 of the safety cap 250 are coupled to each other so that the safety cap 250 can be fixed to the safety holder while surrounding the tip of the needle 210 (see FIG. 6).

Herein, a portion of the safety holder 230 where the fastening protrusion 232 is formed is a bit shrunk before unlatching the safety cap 250, and is mounted in the safety cap 250. However, the portion meets the fastener 252 of the safety cap 250 when the safety cap 250 pops out and is moved upward, and is widen in opposite directions to be coupled to the fastener.

Accordingly, the needle 210 is fully covered with both the safety holder 230 and the safety cap 250, whereby it is possible to prevent the needle from being exposed to the user's field of vision. Further, since the safety cap 250 is fixed, the tip of the needle 210 cannot protrude by an external force, whereby it is possible to prevent needle-stick injuries.

Next, the filter part 300 is mounted between the safety needle part 200 and the main body part 400, and may include a double filter 320 functioning to filter harmful foreign matters contained in the fluid twice.

The double filter 320 is coupled with the barrel 410 in which the piston 420 mounted, and the double filter 320 is provided with an inlet port 321a through which the fluid is introduced in the barrel 410, and an outlet port 321b through which the fluid in the barrel 410 is discharged, thereby performing double filtering.

In other words, when the piston 420 is pulled out in order to introduce the fluid in the barrel 410, the fluid is introduced in the barrel 410 through the needle 210 via the inlet port 321a (see FIG. 7a).

On the contrary, when the piston 420 is pushed to inject the fluid in the barrel 410 into a patient, the fluid is discharged through the outlet port 321b (see FIG. 7b).

More preferably, the filter part 300 includes: a filter housing 310 configured such that a first end thereof is connected with the safety needle part 200 and a second end thereof is coupled with the barrel 410; the double filter 320 mounted in the filter housing 310, and provided with the inlet port 321a and the outlet port 321b that are opened in opposite directions; and a filter 322 provided in each of the inlet port 321a and the outlet port 321b.

More preferably, the filter 322 should have a filtering ability capable of filtering out foreign matters having a size of 5 μm or more.

Meanwhile, more preferably, the double filter 320 is made of silicone, and is configured such that a first side thereof is the inlet port 321a and a second side thereof is the outlet port 321b. The double filter 320 may be integrally provided by injection or may be separately provided.

Further, each of the inlet port 321a and the outlet port 321b is provided with a valve 323 that is opened in only one direction, and two valves are opened in opposite directions. Further, the filter 322 is provided to be spaced apart from each valve 323.

More preferably, when the double filter 320 is the integral double filter, a part of the portion to be the valve 323 is cut, and when the double filter is the separate double filter, the separate valve is assembled at a corresponding location and opens in only one direction due to the coupling structure.

Meanwhile, to stably mount the double filter 320 in the filter housing 310, a support 330 may be provided in the filter housing 310 to support the double filter 320.

As described above, since the safety syringe according to the first embodiment of the present invention is configured such that the fluid is filtered twice by the filter part 300 before injection, even if particulate matters harmful to the human body are present in the fluid, it is filtered, thereby preventing medical accidents.

FIGS. 4a and 5a show the safety syringe according to the first embodiment of the present invention in a state where the needle 210 is capped with the needle cap 100 before use of the syringe.

Next, FIGS. 4b and 5b show a state where the needle cap 100 is removed to use the syringe.

Next, FIGS. 4c and 5c show a state where the fluid is introduced. Here, the fluid is filtered once by the filter 322 of the double filter 320, and is introduced in the barrel 410 through the inlet port 321a.

Next, FIGS. 4d and 5d show a state where the fluid is injected. Here, the fluid is filtered once again by the filter 322 of the double filter 320, and is discharged to the needle 210 through the outlet port 321b.

Lastly, FIGS. 4e and 5e show a state where the safety cap 250 is unlatched after use of the syringe. To be more specific, when the latching means 251 of the safety holder 230 is pressed or the safety cap 250 is rotated to unlatch the latching means 251 from the latching protrusion 231, the safety cap 250 pops out by the elastic force of the elastic body 240. Here, the safety cap 250 is fixed while popping out when the fastener 252 of the safety cap 250 and the fastening protrusion 232 of the safety holder 230 are coupled to each other.

Meanwhile, the safety needle part 200 and the filter part 300 should not be separated once coupled to each other. Referring to FIG. 8, a serration 233 is formed on an inner surface of the first end of the safety holder 230, and a concave-convex portion is formed on an outer surface of the first end of the filter housing 310 to correspond to the serration, whereby the safety holder and the filter housing are coupled to each other, and after being coupled, they are not separated from each other by not being rotated in opposite directions.

More preferably, a lower portion of the safety holder 230 is provided with an anti-vertical moving means 234, and an upper outer surface of the filter housing 310 is provided with an anti-vertical moving protrusion 312, whereby the safety holder and the filter housing are coupled to each other, and after being coupled, they are not separated from each other by not being moved vertically.

Accordingly, once the safety needle part 200 and the filter part 300 are coupled to each other, they are not separated from each other, whereby it is possible to fundamentally prevent some medical staff from reusing some parts of the syringe.

Lastly, the main body part 400 includes: the barrel 410 receiving the fluid introduced through the needle; the piston 420 mounted in the barrel and provided with the insertion part 421 at the fore end thereof to push out the fluid by being inserted into the luer 412 at the upper portion of the barrel;

and a gasket 430 of elastic material surrounding a fore end of the piston with the insertion part 421 penetrating therethrough.

Accordingly, as in the conventional syringe, in the safety syringe of the present invention, not only the gasket 430 pushes out the fluid by coming into contact with the barrel 410, but also the insertion part 421 is inserted into the luer 412 to push the fluid out to the lower end of the double filter 320, it is possible to prevent waste of the fluid by remaining in the barrel 410.

Referring to FIG. 9, the insertion part 421 includes a cylindrical body 421a with a conical tip 421b formed at a first end of the cylindrical body 421a, such that a longitudinal section of the insertion part is in the form of an arrow, and a stop step 412a is formed inside the luer 412.

Herein, a diameter of a bottom of the conical tip 421b is larger than that of an opening of the luer 412 from which the conical tip 421b is inserted.

When manufacturing the safety syringe of the present invention, the bottom of the conical tip 421b is disposed at a location below the stop step 412a. Accordingly, the piston 420 can be pulled backward to inject the fluid.

However, when the piston 420 is pressed forward strongly, the bottom of the conical tip 421b passes through the stop step 412a and is stopped by the stop step 412a. Accordingly, even if the user pulls the piston 420 backward, the piston 420 is not moved, whereby it is possible to prevent reuse of the syringe.

More preferably, the gasket 430 is formed with at least one coupling groove 431 thereinside, and the fore end of the piston 420 is formed with a coupling protrusion 422 corresponding to the coupling groove 431, whereby the coupling groove 431 and the coupling protrusion 422 are engaged with each other.

Accordingly, after the bottom of the conical tip 421b is stopped by the stop step 412a, when the piston 420 is pulled backward strongly, the thinnest portion of the piston 420 below the insertion part 421 is broken, whereby it is possible to prevent reuse of the syringe.

Meanwhile, the filter part 300 and the main body part 400 should not be separated once coupled to each other. Referring to FIG. 10, a serration 311 is formed on an inner surface of the first end of the filter housing 310, and a concave-convex portion is formed on an outer surface of a locking portion 411 provided at the first end of the barrel 410 to correspond to the serration, whereby the filter housing and the barrel are coupled to each other, and after being coupled, they are not separated from each other by not being rotated in opposite directions.

Accordingly, once the filter part 300 and the main body part 400 are coupled to each other, they are not separated from each other, whereby it is possible to fundamentally prevent some medical staff from reusing some parts of the syringe.

Further, the filter housing 310 is coupled with the locking portion 411 having a diameter smaller than that of the body part of the barrel 410, so a diameter of the filter part 300 is reduced compared to the case when the filter housing is coupled with the body part of the barrel 410. Accordingly, it is possible to further reduce the amount of the fluid remaining in the barrel, and it is possible to make the syringe slim.

Figure 11:
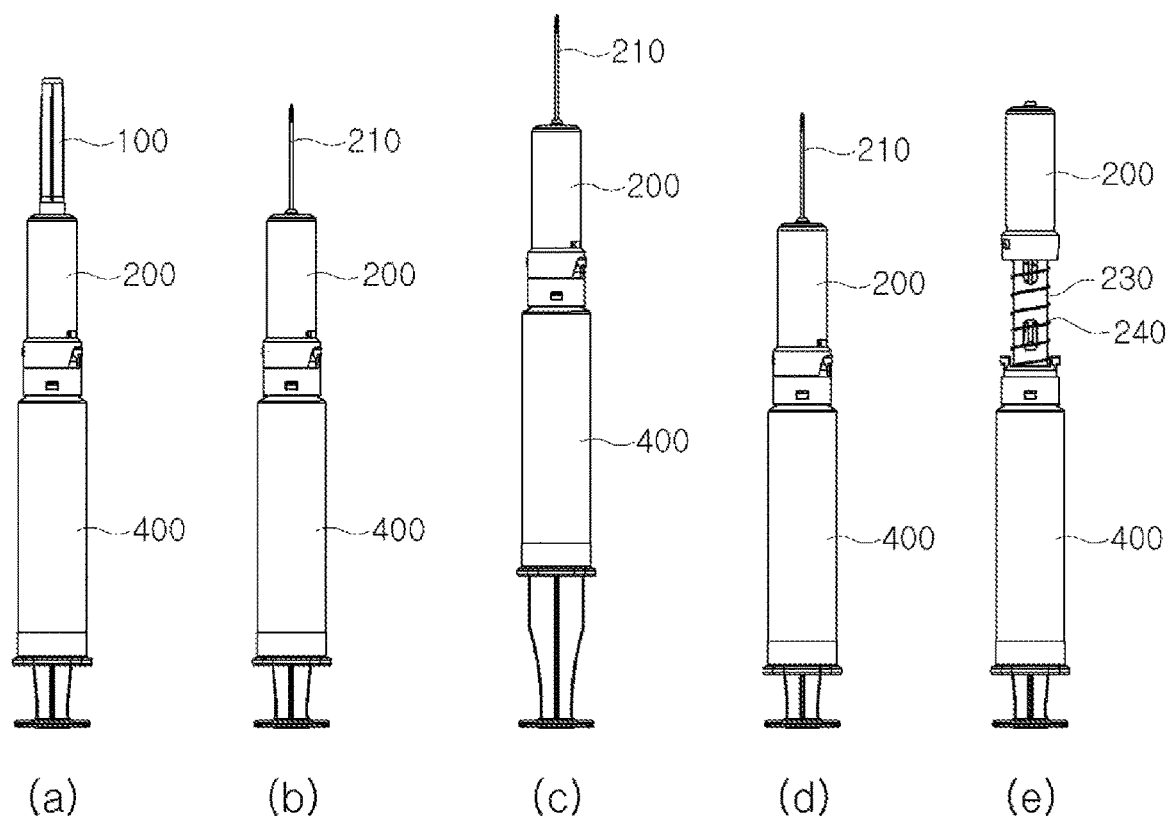
FIG. 11 shows use state views of a safety syringe according to a second embodiment of the present invention.
Figure 12:
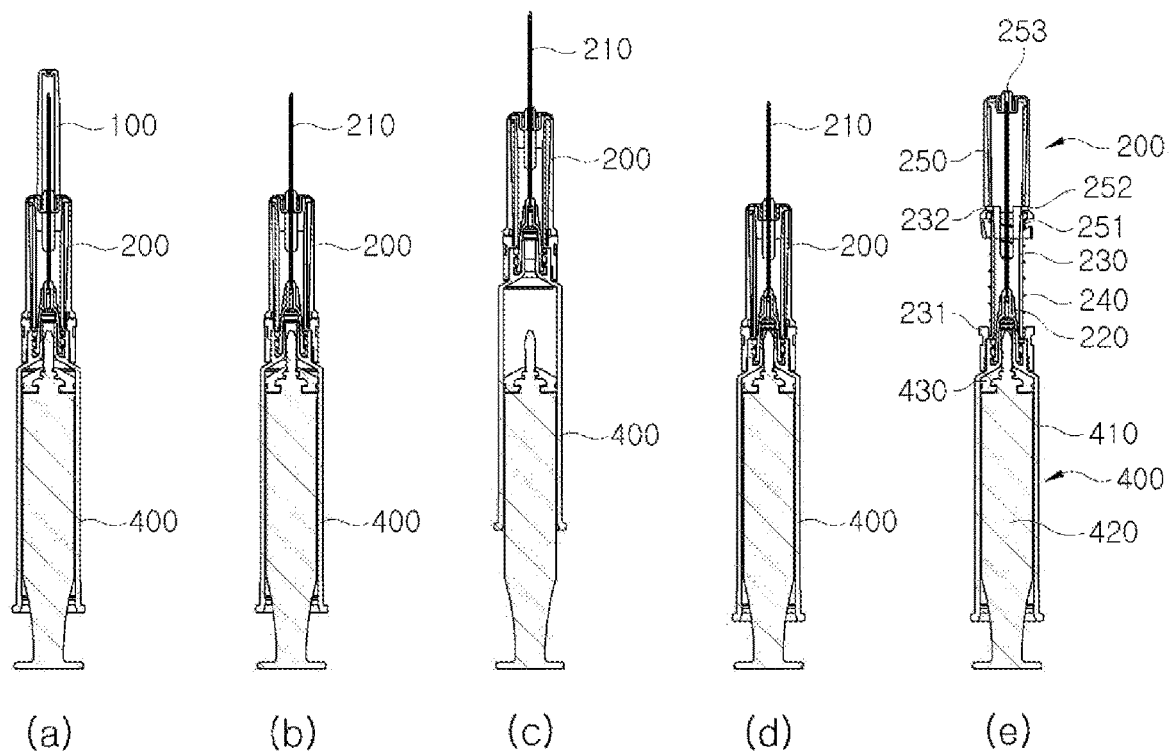
FIG. 12 shows sectional use state views of the safety syringe according to the second embodiment of the present invention.

Next, FIGS. 11 and 12 show use state views and sectional use state views of the safety syringe according to a second embodiment of the present invention. Referring to FIGS. 11 and 12, the safety syringe includes the safety needle part 200 and the main body part 400, excluding the filter part 300.

In FIGS. 11 and 12, FIGS. 11a and 12a show the safety syringe of the present invention in a state where the needle is capped with the needle cap 100 before use of the syringe. FIGS. 11b and 12b show a state where the needle cap 100 is removed to use the syringe. FIGS. 11c and 12c show a state where the fluid is introduced. FIGS. 11d and 12d show a state where the fluid is injected. Lastly, FIGS. 11e and 12e show a state where the safety cap 250 is unlatched after use of the syringe.

The safety syringe according to the second embodiment of the present invention is not provided with the filter part 300, so it cannot filter foreign matters in the fluid. However, the safety syringe is provided with the safety needle part 200, whereby it is possible to prevent needle-stick injuries.

Further, the serration 233 is formed on the inner surface of the first end of the safety holder 230, and the concave-convex portion is formed on the outer surface of the locking portion 411 provided at the first end of the barrel 410 to correspond to the serration, whereby the safety holder and the barrel are coupled to each other, and after being coupled, they are not separated from each other by not being rotated in opposite directions.

Accordingly, the safety syringe according to the second embodiment of the present invention is capable of preventing some medical staff from reusing some parts of the syringe.

Figure 13:
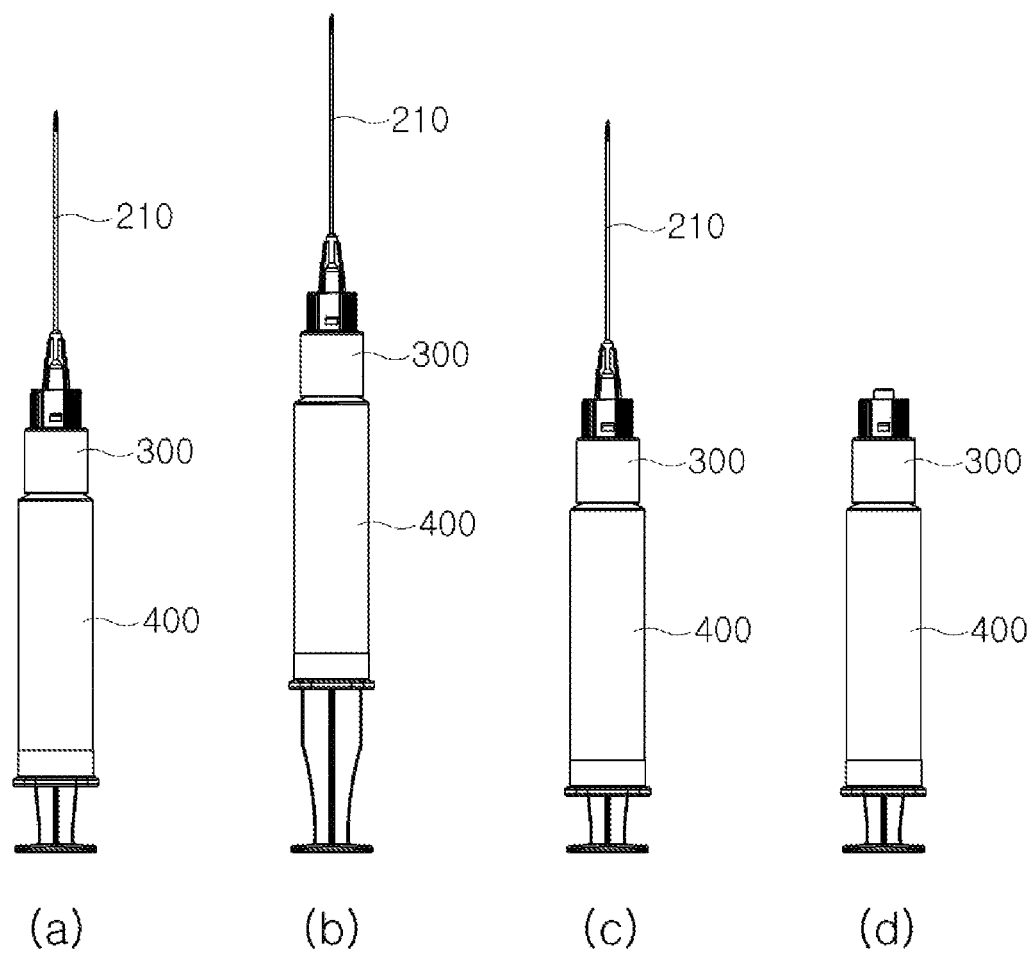
FIG. 13 shows use state views of a safety syringe according to a third embodiment of the present invention.
Figure 14:
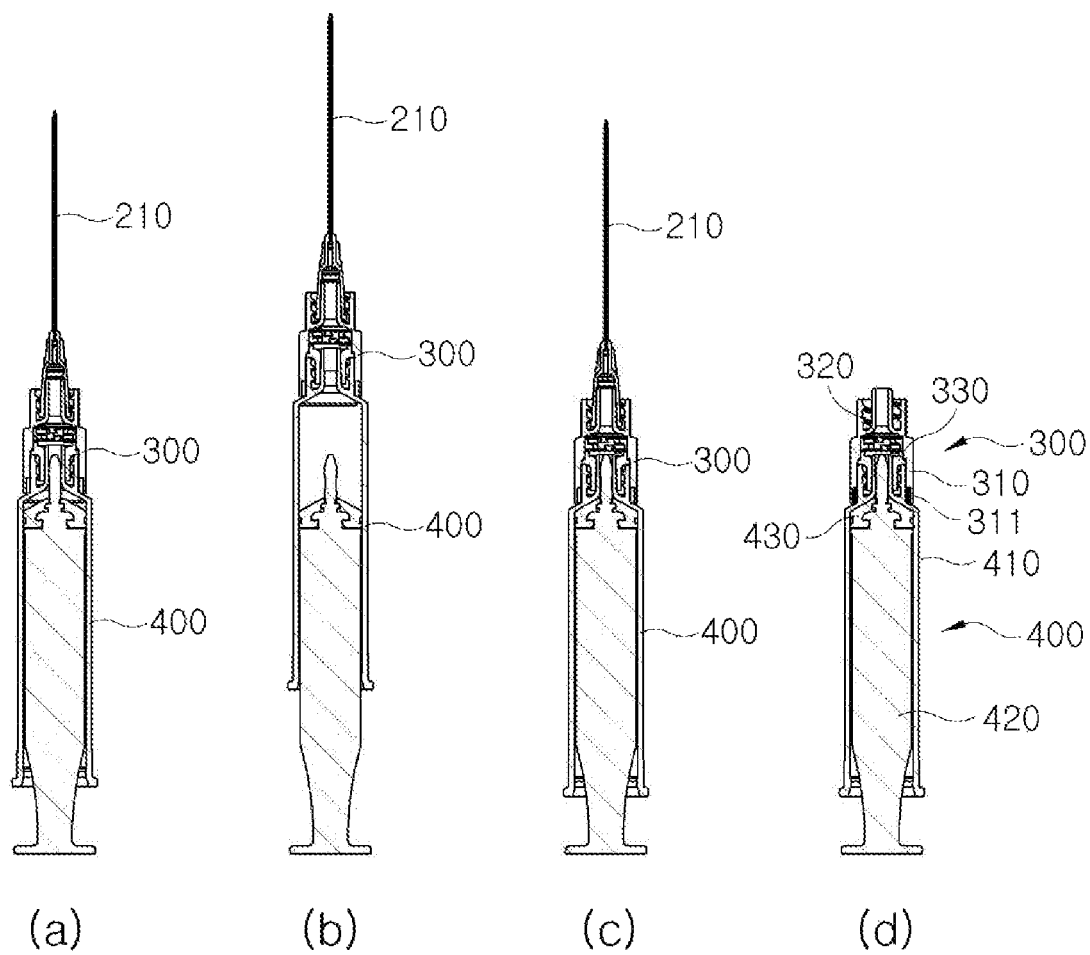
FIG. 14 shows sectional use state views of the safety syringe according to the third embodiment of the present invention.

Next, FIGS. 13 and 14 show use state views and sectional use state views of the safety syringe according to a third embodiment of the present invention. Referring to FIGS. 13 and 14, the safety syringe includes the filter part 300 and the main body part 400, excluding the safety needle part 200.

The safety syringe according to the third embodiment of the present invention, unlike the safety syringe according to the first and the second embodiments, is not provided with the safety needle part 200, whereby it is impossible to connect a general syringe needle (hub) to the syringe.

In FIGS. 13 and 14, FIGS. 13a and 14a show a state where the needle cap 100 is removed. FIGS. 13b and 14b show a state where the fluid is introduced. FIGS. 13c and 14c show a state where the fluid is injected. Lastly, FIGS. 13d and 14d show a state where the needle is removed after use of the syringe.

The safety syringe according to the third embodiment of the present invention is not provided with the safety needle part 200, so it cannot prevent needle-stick injuries.

However, the safety syringe is provided with the filter part 300, whereby it is possible to filter foreign matters in the fluid.

Further, the serration 311 is formed on the inner surface of the first end of the filter housing 310, and the concave-convex portion is formed on the outer surface of the locking portion 411 provided at the first end of the barrel 410 to correspond to the serration, whereby the filter housing and the barrel are coupled to each other, and after being coupled, they are not separated from each other by not being rotated in opposite directions.

Accordingly, the safety syringe according to the third embodiment of the present invention is capable of preventing some medical staff from reusing some parts of the syringe.

Further, since the safety syringe in the second and the third embodiments includes the same main body part 400 as in the first embodiment, it is possible to reduce the amount of the fluid remaining in the barrel thanks to the shape of the piston 420, and it is possible to prevent reuse of the syringe.

As described above, the safety syringe of the present invention can provide four major advantages: it is possible to solve the problem that the user is infected by being pricked by the needle of the used syringe; it is possible to prevent medical accidents by injecting the fluid after filtering the fluid twice; and it is possible to prevent reuse of the used syringe. Further, since the safety syringe is divided into the following three parts, the safety needle part, the filter part, and the main body part, it is possible to assemble only necessary parts to produce the safety syringe according to customer's request.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A safety syringe comprising: a safety needle part; a filter part having a first end thereof coupled with the safety needle part and configured to filter fluid introduced or discharged through a needle of the safety needle part; and a main body part comprising a barrel with a piston mounted therein, the main body part having a first end thereof coupled with the filter part wherein the filter part includes: a filter housing configured such that a first end thereof is connected with the safety needle part and a second end thereof is coupled with the main body part; and a double filter mounted in the filter housing, the double filter provided with an inlet port configured for the introduction of the filtered fluid into the barrel, and an outlet port configured for the discharge of the filtered fluid out of the barrel thereby performing double filtering, the inlet port and the outlet port being configured to open in opposite directions; and a second filter provided in the inlet port and a third filter provided in the outlet port.

2. The safety syringe of claim 1, wherein the double filter is made of silicone and each of the inlet port and the outlet port is provided with a valve configured to be opened in one direction, wherein each of the valves are configured to be integrally or separately formed.

3. The safety syringe of claim 1, wherein a serration is formed on an inner surface of the first end of the filter housing and a concave-convex portion corresponding to the serration is formed on an outer surface of a locking portion provided at a first end of the barrel, whereby when the filter housing and the barrel are coupled to each other the filter housing and the barrel are prevented from being rotated in opposite directions.

4. The safety syringe of claim 1, wherein a serration is formed on an inner surface of a first end of the safety holder and a concave-convex portion corresponding to the serration is formed on an outer surface of the first end of the filter housing, whereby when the safety holder and the filter housing are coupled to each other the safety holder and the filter housing are prevented from being rotated in opposite directions.

5. The safety syringe of claim 4, wherein a lower portion of the safety holder is provided with an anti-vertical moving means and an upper outer surface of the filter housing is provided with an anti-vertical moving protrusion, whereby when the safety holder and the filter housing are coupled to each other the safety holder and the filter housing are prevented from being moved vertically.

6. The safety syringe of claim 1, wherein the safety needle part is provided with a safety cap that is configured to pop out by an elastic force of an elastic body connected thereto when the safety cap is unlatched and configured to be fixed when the safety cap surrounds a needle tip of the needle, the safety needle part also including: a needle hub fastening a lower portion of the needle; a safety holder with the needle hub mounted therein, the safety holder having a lower outer surface provided with a latching protrusion and an upper outer surface provided with a fastening protrusion; wherein the safety cap has a latching means that corresponds to the latching protrusion provided at a first end thereof, a fastener that corresponds to the fastening protrusion provided above the latching means, and a through-hole provided at a second end thereof to allow the needle to pass therethrough; and wherein the elastic body is configured such that a first end thereof is connected with the safety holder and a second end thereof is connected with the safety cap.

7. The safety syringe of claim 6, wherein the safety cap is configured to be unlatched by disengaging the latching means from the latching protrusion by a pressing force pressing the latching protrusion or by rotating the safety cap.

8. The safety syringe of claim 6, wherein as the safety cap is configured to pop out, the fastening protrusion of the safety holder and the fastener of the safety cap are coupled to each other such that the safety cap is fixed to the safety holder while surrounding the needle tip.

9. A safety syringe comprising: a safety needle part having a needle; a filter part having a first end thereof coupled with the safety needle part and configured to filter fluid introduced or discharged through the needle; and a main body part having a first end thereof coupled with the filter part, wherein the main body part includes: a barrel provided with a luer at a fore end of the barrel, the luer having a smaller diameter than the barrel and communicating with the barrel, the barrel and the luer being capable of receiving a fluid introduced through the needle; a piston mounted in the barrel and provided with an insertion part at a fore end of the piston to push out the fluid by being inserted into the luer, the insertion part substantially conforming to an inner wall of the luer when inserted into the luer; and a gasket of elastic material surrounding the fore end of the piston with the insertion part penetrating therethrough, and wherein the insertion part includes a cylindrical body with a conical tip formed at a first end of the cylindrical body such that a longitudinal section of the insertion part has a pointed end and a diameter of a bottom of the conical tip is larger than a diameter of an opening of the luer from which the conical tip is inserted; wherein a stop step is provided inside the luer such that a diameter of a needle side portion of the luer is larger than a diameter of a barrel side portion of the luer; and wherein when the piston is pressed forward, the bottom of the conical tip is configured to pass through the stop step and when the piston is pulled backward, the bottom of the conical tip is configured to engage the stop step to stop the piston.

10. The safety syringe of claim 9, wherein the gasket is provided with at least one coupling groove thereinside and the fore end of the piston is formed with a coupling protrusion corresponding to the coupling groove, whereby the coupling groove and the coupling protrusion are engaged with each other and wherein a thinnest portion of the piston below the insertion part is configured to be broken after the piston is stopped by the stop step, when the piston is pulled backward.

* * * * *